United States Patent [19]
Gröning et al.

[11] Patent Number: 6,063,939
[45] Date of Patent: May 16, 2000

[54] PROCESS FOR PREPARING UNSATURATED CYCLIC ETHERS

[76] Inventors: Carsten Gröning, Mosbacher Str.29, 68259 Mannheim; Michael Hesse, Weinbiestr.10, 67549 Worms; Daniel Heineke, am Alsterbach 7, 67487 Maikammer; Heinz-Josef Kneuper, Stephanienufer 18, 68163 Mannheim; Gerhard Fritz, Limburgst.23, 67125 Dannstadt-Schauernheim, all of Germany

[21] Appl. No.: 09/226,144

[22] Filed: Jan. 7, 1999

[30] Foreign Application Priority Data

Jan. 29, 1998 [DE] Germany .......................... 198 03 368

[51] Int. Cl.⁷ .................... C07D 309/00; C07D 319/12; C07D 507/02; B01J 27/045
[52] U.S. Cl. .................... 549/356; 549/346; 549/377; 549/507; 549/510; 502/223; 502/74
[58] Field of Search .................... 549/346, 356; 502/44, 223

[56] References Cited

U.S. PATENT DOCUMENTS

| | | | |
|---|---|---|---|
| 2,993,910 | 7/1961 | Dimroth et al. | 260/346.1 |
| 3,817,996 | 6/1974 | Snapp, Jr. | 260/345.1 |
| 5,689,715 | 11/1997 | Crump et al. | 395/750 |

FOREIGN PATENT DOCUMENTS

| | | |
|---|---|---|
| 2 346 943 | 4/1974 | Germany . |
| 195 30993 | 2/1997 | Germany . |

*Primary Examiner*—Amelia Owens

[57] ABSTRACT

Unsaturated cyclic ethers of the formula I

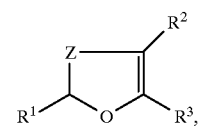
(I)

where

Z is —(CHR⁴)$_q$— or —(CHR⁴)$_q$—O—,
q is 0, 1, 2 or 3 and
R¹,R²,R³,R⁴ are hydrogen or $C_1$–$C_4$-alkyl are prepared by reacting diols of the formula II

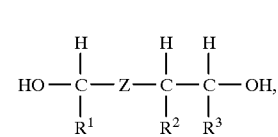
(II)

where Z, R¹, R² and R³ are as defined above, in the liquid phase at from 150 to 300° C. in the presence of a cobalt-containing supported catalyst which has not been activated by reduction before use and comprises cobalt and a noble metal selected from the group consisting of platinum, palladium, rhodium, iridium, ruthenium, osmium, rhenium or a mixture thereof applied by sol impregnation on an inert support, wherein the supported catalyst is doped with sulfur. Sulfur-doped supported catalysts comprising cobalt and noble metals are also provided.

7 Claims, No Drawings

PROCESS FOR PREPARING UNSATURATED CYCLIC ETHERS

The present invention relates to a process for preparing unsaturated cyclic ethers from diols in the liquid phase over supported catalysts comprising cobalt and noble metals and also to novel supported catalysts which comprise cobalt and noble metals and are doped with sulfur.

DE-A-23 46 943 discloses a process for preparing unsaturated cyclic compounds from diols under a stream of hydrogen, in which process mixtures of a copper chromite or copper supported catalyst and a tungstic or heteropolytungstic acid are used as catalysts. The conversions and yields leave something to be desired.

U.S. Pat. No. 2,993,910 discloses a process for preparing dihydrofurans from 1,4-butanediols over cobalt catalysts which have to be reduced with hydrogen at from 300 to 450° C.

DE-A-195 30 993 discloses a process for preparing unsaturated cyclic ethers over platinum-doped, cobalt-containing supported catalysts.

The known catalysts do not have sufficiently high activities and satisfactory operating lives in all applications. In particular, the reproducibility of the catalyst activity for the conversion of 1,5-pentanediol into 3,4-dihydro-2H-pyran is unsatisfactory.

Furthermore, precisely for this reaction, a very low content of the by-product tetrahydropyran in the reaction product is decisive for industrial use of the 3,4-dihydro-2H-pyran. This is necessary for economical purification of the reaction product because the boiling points lie very close together.

It is an object of the present invention to provide a process for preparing unsaturated cyclic ethers from diols, which process makes possible high space velocities over the catalyst and long catalyst operating lives at an increased catalyst activity using readily reproducible catalysts and has a very high selectivity so as to suppress the formation of the by-product tetrahydropyran.

We have found that this object is achieved by a new and improved process for preparing unsaturated cyclic ethers of the formula I

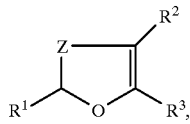

(I)

where

Z is —(CHR$^4$)$_q$— or —(CHR$^4$)$_q$—O—,
q is 0, 1, 2 or 3 and
R$^1$,R$^2$,R$^3$,R$^4$ are hydrogen or C$_1$–C$_4$-alkyl by reacting diols of the formula II

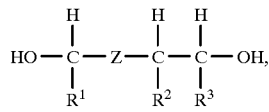

(II)

where Z, R$^1$, R$^2$ and R$^3$ are as defined above, in the liquid phase at from 150 to 300° C. in the presence of a cobalt-containing supported catalyst which has not been activated by reduction before use and comprises cobalt and a noble metal selected from the group consisting of platinum, palladium, rhodium, iridium, ruthenium, osmium, rhenium or a mixture thereof applied by sol impregnation on an inert support, wherein the supported catalyst is doped with sulfur.

The substituents R$^1$, R$^2$, R$^3$, R$^4$, the link Z and the index q in the compounds I and II have the following meanings:

R$^1$, R$^2$, R$^3$, R$^4$ are, independently of one another,
  hydrogen,
  C$_1$–C$_4$-alkyl such as methyl, ethyl, n-propyl, iso-propyl, n-butyl, iso-butyl, sec-butyl and tert-butyl, preferably C$_1$–C$_3$-alkyl such as methyl, ethyl, n-propyl and iso-propyl, particularly preferably methyl and ethyl,
Z is —(CHR$^4$)$_q$— or —(CHR$^4$)$_q$—O—,
q is 0, 1, 2 or 3, preferably 0 or 1, particularly preferably 1.

Suitable diols II are, for example, 1,4-butanediol, 1,5-pentanediol, 1,6-hexanediol, diethylene glycol, preferably 1,5-pentanediol.

Unsaturated cyclic ethers I which can be prepared are, for example, 3,4-dihydro-2H-pyran, 2,3-dihydrofuran and 1,4-dioxane, preferably 3,4-dihydro-2H-pyran.

The process of the present invention can be carried out as follows:

The diol II can be reacted over, in general, from 0.2 to 20% by weight, preferably from 0.3 to 10% by weight, of cobalt-containing supported catalyst at from 150 to 300° C., preferably from 160 to 240° C. The cobalt-containing supported catalyst can be charged initially or added stepwise during the reaction in aliquots of the total amount. The reaction mixture should be stirred uniformly during the reaction and the stirrer speed should be selected so that the catalyst is not excessively stressed mechanically as a result of the stirring energy introduced. The resulting mixture of the unsaturated cyclic ether I and the water of reaction can be distilled off discontinuously, preferably continuously. The unsaturated cyclic ether formed in the reaction can, if desired, be stripped using gases which are inert under the reaction conditions, e.g. nitrogen or argon, to remove the hydrogen formed in the reaction. In continuous operation, the liquid level in the reaction vessel can be maintained by feeding in fresh diol II. The addition of alkali metal compounds and/or alkaline earth metal compounds to lower the content of saturated cyclic ethers which can be separated by distillation from the unsaturated 3,4-dihydro-2H-pyran only with difficulty is not necessary in the process of the present invention.

Suitable sulfur-doped supported catalysts comprising cobalt and noble metals are the oxides of cobalt or metallic cobalt and one or more noble metal elements selected from the group consisting of platinum, palladium, rhodium, iridium, ruthenium, osmium, rhenium or mixtures thereof, preferably platinum, palladium, rhenium or mixtures thereof, particularly preferably platinum, palladium or mixtures thereof, plus, if desired, from 0.001 to 10% by weight, preferably from 0.1 to 5%, by weight, particularly preferably from 0.5 to 3% by weight, of basic alkali metal salts, alkaline earth metal salts, scandium, vanadium, chromium, manganese, iron, nickel, copper, zinc, germanium, tin, lead, antimony, bismuth or mixtures thereof (compound A), preferably lithium, potassium, sodium, calcium, strontium, barium, manganese, iron, nickel, copper, zinc, tin, antimony or a mixture thereof, particularly preferably potassium, sodium, manganese, iron, nickel, copper, zinc or a mixture thereof, on a porous support.

The proportion by weight of cobalt (oxide) in the supported catalyst is generally from 1 to 70% by weight, preferably from 5 to 50% by weight, particularly preferably from 10 to 40% by weight.

The proportion by weight of the elements selected from the group consisting of platinum, palladium, rhodium, iridium, ruthenium, osmium and rhenium, preferably platinum, palladium and rhenium, is from 0.001 to 2% by weight, preferably from 0.05 to 1% by weight, particularly preferably from 0.01 to 0.5% by weight, based on the supported catalyst.

The proportion by weight of sulfur (calculated as S) is from 0.015 to 2% by weight, preferably from 0.1 to 1% by weight, particularly preferably from 0.3 to 0.6% by weight, based on the supported catalyst.

To determine the sulfur content of the catalyst, the supported catalyst is dissolved in hydrochloric acid and treated with hypophosphorous acid. The hydrogen sulfide formed is stripped by means of a stream of $N_2$, absorbed in ammoniacal cadmium acetate solution and determined iodometrically.

The supported catalysts generally have a weight ratio of cobalt (oxide) to noble metal of from 10:1 to 10,000:1 and of noble metal to sulfur of from 100:1 to 1:100.

Suitable supports are inert supports such as $SiO_2$, $Al_2O_3$, $TiO_2$, $ZrO_2$, zeolites of all types such as small-pored zeolites, e.g. A-zeolite, intermediate-pored zeolites, e.g. ZSM-5, ZSM-11, ferrierite, large-pored zeolites, e.g. faujasite, β-zeolites, mordenite, offretite, hydrothermally prepared phosphates such as AlPO and SAPO, activated carbons or alkaline earth metal oxides, preferably $SiO_2$, $ZrO_2$ and zeolites, particularly preferably $SiO_2$. The weight ratio of cobalt (oxides) to the $SiO_2$ in the supported catalyst is generally from 1:20 to 1:1.

The supported catalysts generally have a BET surface area of from 1 to 600 $m^2/g$, preferably from 10 to 500 $m^2/g$, particularly preferably from 50 to 400 $m^2/g$.

The porosity of the supported catalysts is generally from 0.01 to 1.5 ml/g, preferably from 0.1 to 1.2 ml/g, particularly preferably from 0.2 to 1 ml/g.

The supported catalysts used according to the present invention are prepared by applying first cobalt then the noble metal in the form of a sol to the support and subsequently doping with sulfur.

The preparation of cobalt-containing supported catalysts is generally known. An advantageous method is impregnation of the porous support material with a soluble cobalt compound (e.g. a nitrite, nitrate, sulfite, sulfate, carbonate, hydroxide or carboxylate, halide, halite, halate, etc.), if desired simultaneously or successively with a likewise soluble compound A (e.g. as nitrite, nitrate, sulfite, sulfate, carbonate, hydroxide, carboxylate, halide, halite, halate, etc.) and subsequent thermal decomposition of the anion to the oxide. A further possible way is mixing a cobalt compound with the support material (dry or in suspension, in particular by spray drying), if desired simultaneously with a chemical compound A, compaction of the material (e.g. by kneading, if desired with addition of a suitable shaping aid), shaping by extrusion, drying and subsequent calcination at from 200 to 1300° C., preferably from 300 to 1000° C., particularly preferably from 400 to 800° C.

The noble metal selected from the group consisting of platinum, palladium, rhodium, iridium, ruthenium, osmium, rhenium or a mixture thereof is then applied to the support by spraying the still hot support or impregnating the support with a previously prepared sol; if appropriate, the catalyst composition which has been agglomerated as a result of the previous impregnation is comminuted before application of the noble metal.

The noble metal sol is a colloidal material and can be prepared by known methods, e.g. starting from metal salts in which the noble metal is present in an oxidation state of greater than zero. It is possible to use, for example, aqueous solutions of the chlorides, acetates or nitrates of the metal. However, it is also possible to use other noble metal salts; there is no restriction in respect of the anion. Reducing agents which can be used are organic compounds such as ethanol, methanol, carboxylic acids and their alkali metal salts and also inorganic compounds such as $N_2H_4$ or $NaBH_4$. Preference is given to using hydrazine $N_2H_4$ and ethanol. The particle size of the metal particles in the sol here depends on the strength of the reducing agent used and on the metal salt employed. The sols can be stabilized by addition of organic polymers such as polyamines, polyvinylpyrrolidone or polyacrylates, with preference being given to polyvinylpyrrolidone PVP. However, the preparation of the sol can also be carried out by other methods described in the literature. For example, Bönnemann et al. (Angew. Chemie, 103 (1991), 1344) describe the preparation of stable metal sols by reduction of metal salts with $(C_8H_{17})_4N$ [$BEtH_3$].

The sols can be applied to the support by various techniques which influence the distribution of the active component. To produce thin shells of the active component for the entire extrudate cross section, the sol is sprayed onto an indirectly heated support. The procedure is to place the support in a rotatable, heatable pelletizing pan and heat it to from 80 to 200° C. by means of a hot air blower. While the pan is being rotated, the sol is sprayed onto the support. The rotation of the pan ensures mixing of the support particles, e.g. extrudates or granules. On contact with the hot support, the liquid in the sol evaporates and the active component remains on the support. This application technique forms catalysts in which the active component is applied in thin layers, generally of less than 50 µm, to the support. The particle size of the noble metal agglomerates is generally of the same order of magnitude as in the sol. The catalyst is then dried at a temperature which does not exceed 150° C.

Another technique of applying the active component comprises impregnating the support with a metal sol in an amount corresponding to the previously determined water absorption of the support, which essentially corresponds to its pore volume. After allowing excess liquid to drip from the support, the latter is then dried at a temperature which does not exceed 150° C. Catalysts prepared in such a way surprisingly have the active component likewise present in a very thin layer. In this case, however, when macroporous supports are used the active component is present in greater concentration in the macropores which are accessible from the outside, while when the sol is sprayed on the active component is distributed essentially uniformly in micropores and macropores.

In a third step of catalyst production, the supported catalyst comprising cobalt and noble metal is subsequently doped with sulfur; if desired, the catalyst material agglomerated as a result of the previous sol impregnation is comminuted beforehand. The doping of the supported catalyst with sulfur is carried out by impregnating the support with an aqueous or water-containing solution comprising at least one inorganic and/or organic sulfur compound of a formally negative oxidation state of sulfur, for example the formal negative oxidation state (−2) of sulfur, or a solution in an organic solvent, with the use of an aqueous solution being preferred. The water-containing solutions can further comprise organic solvents in addition to water. Suitable organic solvents are polar protic or aprotic organic solvents, for example alcohols such as methanol.

Among the sulfur compounds having a formally negative oxidation state which are suitable for doping the catalysts used according to the present invention with sulfur, preference is given to ammonium sulfide, thiourea and mercaptopyrimidines, for example 4-amino-2-mercaptopyrimidine.

The impregnation can be achieved by treating the support material with a supernatant solution of the sulfur compound; it is particularly advantageously carried out by addition of the solution comprising the sulfur compound to the support in a rotating drum, advantageously using an amount of solution which corresponds to the pore volume of the support.

After drying and, if desired, calcination, generally at from 250 to 500° C., preferably from 300 to 400° C., the catalyst can be used in the process of the present invention.

It is advantageous that the catalysts do not have to be activated by treatment with hydrogen or other reducing agents such as hydrazine before they are employed in the process of the present invention.

The unsaturated cyclic ethers I are valuable protective groups for alcohols.

EXAMPLES

Preparation of the Catalysts A and B 16.7 l of a solution of 12.61 kg of $Co(NO_3)_2.6H_2O$ (corresponding to 3.25 kg of CoO) in water were stirred with 10 kg of $SiO_2$ powder (water absorption=1.85 ml/g) for about 2 hours, dried at 120° C. for 16 hours and calcined at 500° C. for 2 hours.

The material was then impregnated with 15.8 l of a noble metal sol prepared by mixing 22.3 g of platinum nitrate in 4.5 l of distilled water with 32 g of polyvinylpyrrolidone and 1.93 l of ethanol, refluxing for 4 hours and diluting with water; the impregnated material was subsequently dried at 100° C. under reduced pressure and calcined at 500° C. under an $N_2$ atmosphere for 2 hours. The catalyst prepared in this way contains 0.12% by weight of $PtO_2$.

4.6 g of these cobalt- and platinum-containing materials were then impregnated with a solution of $(NH_4)_2S$ in water, subsequently dried at 100° C. under reduced pressure and calcined at 350° C. for 2 hours.

Further details regarding the preparation and properties of the catalysts A and B are shown in Table 1.

TABLE 1

| Catalyst | Amount of noble metal sol [ml] | Noble metal content [% by weight] | $(NH_4)_2S$ [g] | Sulfur content [% by weight] |
| --- | --- | --- | --- | --- |
| A | 15800 | 0.10 | 0.04 | 0.34 |
| B | 15800 | 0.10 | 0.06 | 0.38 |

Preparation of the Catalyst C 3400 ml of a solution of 3.25 kg of $Co(NO_3)_2.6H_2O$ in water were stirred with 2.5 kg of $SiO_2$ powder (water absorption=1.5 ml/g) for about 2 hours, dried at 120° C. for 16 hours and calcined at 500° C. for 2 hours.

This material was then impregnated with 2.9 l of a noble metal sol prepared by mixing 14.2 g of platinum nitrate in 4.5 l of distilled water with 32 g of polyvinylpyrrolidone and 1.93 l of ethanol and refluxing for 4 hours; the impregnated material was subsequently dried at 100° C. under reduced pressure and calcined at 500° C. under an $N_2$ atmosphere for 2 hours. The catalyst prepared in this way contains 0.12% by weight of $PtO_2$.

4.6 g of this cobalt- and platinum-containing material were then impregnated with a solution of $(NH_4)_2S$ in water, subsequently dried at 100° C. under reduced pressure and calcined at 350° C. for 2 hours.

Further details regarding the preparation and properties of the catalyst C are shown in Table 2.

TABLE 2

| Catalyst | Amount of noble metal sol [ml] | Noble metal content [% by weight] | $(NH_4)_2S$ [g] | Sulfur content [% by weight] |
| --- | --- | --- | --- | --- |
| C | 2900 | 0.10 | 0.04 | 0.34 |

Comparative Catalysts CA and CB (As Described in DE 19530993)

555 ml of a solution of 291.3 g of $Co(NO_3)_2.6H_2O$ and a metal nitrate in water were stirred with 300 g of $SiO_2$ powder (water absorption=1.85 ml/g) for about 2 hours, dried at 120° C. for 16 hours and calcined at 500° C. for 2 hours. A noble metal sol (0.6 g/l) prepared by mixing a noble metal salt in 700 ml of water with 5 g of polyvinylpyrrolidone and 300 ml of ethanol and refluxing for 4 hours was sprayed onto an amount shown in Table 1 of the above material over a period of 2 hours; the impregnated material was subsequently dried and calcined at 500° C. for 1 hour.

Further details regarding the preparation and properties of the catalysts are shown in Table 3:

TABLE 3

| Catalyst | Noble metal salt [g] | Amount of Co-containing. $SiO_2$ [g] | Amount of noble metal sol [ml] | Noble metal content [% by weight] | Sulfur content [% by weight] |
| --- | --- | --- | --- | --- | --- |
| CA | 1.46 g $Pt(NO_3)_2$ | 310 | 260 | 0.05 | — |
| CB | 1.46 g $Pt(NO_3)_2$ | 328.6 | 548 | 0.1 | — |

Examples 1 to 8

1.5 l of 1,5-pentanediol and 45 g of a catalyst A, B, CA and CB were placed in a reaction flask and heated while stirring to the lower limit of the temperature range, with the reaction starting and evolving hydrogen. The 3,4-dihydro-2H-pyran/water mixture formed was distilled off continuously and the temperature in the liquid phase was regulated during the reaction so that the amount of distillate formed per hour remained constant (40–50 ml). At the same time, 1,5-pentanediol was metered in continuously over the times shown in Table 4 to keep the level in the reaction flask constant. After phase separation of the distillate, 3,4-dihydro-2H-pyran was obtained in the amounts indicated in Table 4.

TABLE 4

| Ex. | Catalyst | Temperature [° C.] | Duration [h] | Yield of DHP [% by weight] | Purity of DHP | THP content | Catalyst activity [kg DPH/kg cat] |
|---|---|---|---|---|---|---|---|
| 1 | A | 170–197 | 200 | 98 | 96 | 1.0 | |
| 2 | A | 170–235 | 780 | 96 | 96 | 0.9 | 534 |
| 3 | B | 170–195 | 200 | 95 | 95 | 1.4 | |
| 4 | B | 170–235 | 740 | 96 | 95 | 1.2 | 525 |
| 5 | CA | 170–212 | 200 | 98 | 97 | 1.5 | |
| 6 | CA | 170–235 | 410 | 98 | 96 | 2.1 | 351 |
| 7 | CB | 170–212 | 200 | 98 | 96 | 1.3 | |
| 8 | CB | 170–235 | 420 | 98 | 95 | 2.0 | 367 |

DHP = 3,4-dihydro-2H-pyran
THP = tetrahydropyran

The experimental results shown in Table 4 clearly demonstrate that the amount of tetrahydropyran in the reaction product was able to be significantly reduced by means of the catalysts A and B used according to the present invention. In addition, the operating life of the catalysts A and B is significantly higher than in the case of the comparative catalysts, as also shown by the long running times of over 200 hours.

Furthermore, the catalysts A and B according to the present invention display good reproducibility.

Example 9

1.5 l of 1,5-pentanediol and b g of catalyst C were placed in a reaction flask and heated while stirring to the lower limit of the temperature range from 170 to 180° C., with the reaction starting and evolving hydrogen. The 3,4-dihydro-2H-pyran/water mixture formed was distilled off continuously and the temperature in the liquid phase was regulated during the reaction so that the amount of distillate obtained per hour remained constant (40–50 ml). At the same time, 1,5-pentanediol was metered in continuously over the times shown in Table 5 to keep the level in the reaction flask constant. Table 5 shows the details of the experimental procedure.

| Catalyst activity (kg DHP/ kg cat) | Duration [h] | Space velocity over the catalyst [g DHP/kg cat/h] | Space-time yield b (g) | Amount of catalyst b (g) | Catalyst concentration |
|---|---|---|---|---|---|
| 567 | 410 | 1383 | 20.7 | 22.5 | 1.478 |
| 800 | 290 | 2759 | 20.7 | 11.25 | 0.744 |
| 834 | 130 | 6415 | 21.4 | 5.00 | 0.322 |

We claim:

1. A process for preparing unsaturated cyclic ethers of the formula I

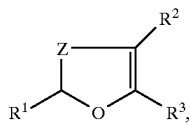

(I)

where

Z is —(CHR$^4$)$_q$— or —(CHR$^4$)$_q$—O—,
q is 0, 1, 2 or 3 and
R$^1$,R$^2$,R$^3$,R$^4$ are hydrogen or C$_1$–C$_4$-alkyl,
by reacting diols of the formula II

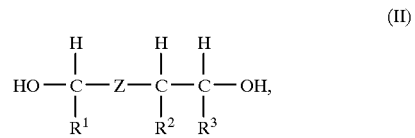

(II)

where Z, R$^1$, R$^2$ and R$^3$ are as defined above, in the liquid phase at from 150 to 300° C. in the presence of a cobalt-containing supported catalyst which has not been activated by reduction before use and comprises cobalt and a noble metal selected from the group consisting of platinum, palladium, rhodium, iridium, ruthenium, osmium, rhenium or a mixture thereof applied by sol impregnation on an inert support, wherein the supported catalyst is doped with sulfur.

2. A process for preparing unsaturated cyclic ethers as claimed in claim 1, wherein the cobalt-containing supported catalyst comprises from 1 to 70% by weight of cobalt, from 0.001 to 2% by weight of one or more noble metals and from 0.015 to 2% by weight of sulfur.

3. A process for preparing unsaturated cyclic ethers as claimed in claim 1, wherein the sulfur is applied by impregnating the catalyst with an aqueous or water-containing solution comprising an inorganic or organic sulfur compound having a formally negative oxidation state of the sulfur or a mixture thereof or a solution in an organic solvent.

4. A process for preparing unsaturated cyclic ethers I as claimed in claim 1, wherein the cobalt-containing supported catalyst comprises from 0.001 to 10% by weight of a basic alkali metal salt or alkaline earth metal salt or a mixture thereof, based on the total metal content.

5. A process for preparing unsaturated cyclic ethers I as claimed in claim 1, wherein the cobalt-containing supported catalyst comprises from 0.001 to 10% by weight of scandium, vanadium, chromium, manganese, iron, nickel, copper, zinc, germanium, tin, lead, antimony, bismuth or a mixture thereof, based on the total metal content.

6. A process for preparing unsaturated cyclic ethers as claimed in any of claims 1, wherein 1,5-pentanediol is converted into 3,4-dihydro-2H-pyran.

7. A cobalt-containing supported catalyst which comprises cobalt and a noble metal selected from the group consisting of platinum, palladium, rhodium, iridium, ruthenium, osmium, rhenium or a mixture thereof applied by sol impregnation on an inert support, is doped with sulfur and is not activated by reduction before use.

* * * * *

UNITED STATES PATENT AND TRADEMARK OFFICE
CERTIFICATE OF CORRECTION

PATENT NO.: 6,063,939

DATED: May 16, 2000

INVENTOR(S): GROENING et al.

It is certified that error appears in the above-identified patent and that said Letters Patent is hereby corrected as shown below:

Col. 8, lines 60-65, delete claim 7.

Signed and Sealed this

Thirteenth Day of March, 2001

*Attest:*

NICHOLAS P. GODICI

*Attesting Officer*   *Acting Director of the United States Patent and Trademark Office*